United States Patent
Bova et al.

(10) Patent No.: US 8,099,152 B2
(45) Date of Patent: Jan. 17, 2012

(54) SYSTEMS AND METHODS FOR PLANNING MEDICAL PROCEDURES AND DESIGNING MEDICAL DEVICES BASED ON ANATOMICAL SCAN DEFORMATIONS

(75) Inventors: Frank J. Bova, Gainesville, FL (US); William A. Friedman, Gainesville, FL (US)

(73) Assignee: Univeristy of Florida Research Foundation, Inc., Gainesville, FL (US)

( * ) Notice: Subject to any disclaimer, the term of this patent is extended or adjusted under 35 U.S.C. 154(b) by 865 days.

(21) Appl. No.: 11/884,631

(22) PCT Filed: Feb. 17, 2006

(86) PCT No.: PCT/US2006/005633
§ 371 (c)(1), (2), (4) Date: Jan. 16, 2008

(87) PCT Pub. No.: WO2006/089112
PCT Pub. Date: Aug. 24, 2006

(65) Prior Publication Data
US 2008/0167547 A1    Jul. 10, 2008

Related U.S. Application Data

(60) Provisional application No. 60/653,724, filed on Feb. 17, 2005.

(51) Int. Cl.
*A61B 5/05* (2006.01)

(52) U.S. Cl. .......... 600/424; 600/407; 600/425
(58) Field of Classification Search .......... 600/424, 600/425; 345/646
See application file for complete search history.

(56) References Cited

U.S. PATENT DOCUMENTS

| | | | |
|---|---|---|---|
| 4,977,505 A | 12/1990 | Pelizzari et al. | |
| 5,961,454 A | 10/1999 | Kooy et al. | |
| 6,006,126 A | 12/1999 | Cosman | |
| 7,103,399 B2 * | 9/2006 | Miga et al. | 600/425 |
| 7,787,932 B2 * | 8/2010 | Vilsmeier et al. | 600/424 |
| 2001/0021806 A1 | 9/2001 | Gueziec et al. | |

OTHER PUBLICATIONS

International Search Report and Written Opinion, dated Nov. 7, 2006.

* cited by examiner

*Primary Examiner* — Michael Rozanski
(74) *Attorney, Agent, or Firm* — Thomas, Kayden, Horstemeyer & Risley, LLP

(57) ABSTRACT

A method of formulating a patient-specific plan for a diagnostic or therapeutic procedure performed upon a patient is provided. The method includes obtaining a standard plan based upon a scan of an anatomy of a standard anatomic specimen, the scan defining a standard scan. The method also includes scanning the patient to obtain a patient-specific scan of an anatomy of the patient. Additionally, the method includes morphing the standard scan to the anatomy of the patient by mapping the standard scan to the patient-specific scan. The method further includes determining the patient-specific plan by modifying the standard plan based upon the mapping.

20 Claims, 5 Drawing Sheets

SYSTEMS AND METHODS FOR PLANNING MEDICAL PROCEDURES AND DESIGNING MEDICAL DEVICES BASED ON ANATOMICAL SCAN DEFORMATIONS

FIELD OF THE INVENTION

This invention relates generally to the fields of medicine, including radiology and surgery. More particularly, the invention relates to methods and devices for formulating medical procedures and designing medical devices.

BACKGROUND

Many therapeutic as well as diagnostic procedures require the identification of a targeted region of the anatomy of a patient. Examples of such procedures include performing a biopsy on the patient, placing a shunt catheter within the patient, obtaining an image of the patient through diagnostic imaging, and inserting a pedicle screw within the patient. Typically, the planning of either a diagnostic or therapeutic procedure entails examining patient data obtained, generally, through an imaging scan, identifying specific target structures in the image or images, and then deciding upon a plan for effecting the procedure.

An increasing number and variety of clinical procedures utilize image guides. Such image guides include image guides for performing biopsies, inserting shunts, and attaching pedicle screws. Planning diagnostic and therapeutic procedures that utilize such guides typically entails selecting an appropriate entrance point into and precise trajectory of the image guide within the body of the patient. As with medical procedure planning generally, the task of planning a procedure that utilizes an image guide is complicated by the fact that the effectiveness of the procedure usually depends critically on choosing an image guide that closely aligns with the particular anatomical features of the patient's body.

Although the same procedure may be carried out again and again in clinical practice, the only guidance that a clinician typically has in planning the procedure is the clinician's own personal experience. For example, if the procedure is the placing of a pedicle screw within a patient, the clinician usually must identify the exact placement entry point of the screw and its path of trajectory for each patient anew. Moreover, even if a particular clinician has performed the procedure many times in the past, the clinician typically only has his or her own experience from which to draw; there generally is no existing mechanism by which the clinician can leverage the experience derived from other clinicians who have performed the procedure. Nor is there any efficient mechanism by which the clinician can obtain a first, best guess at how to proceed in order to save valuable time in the initial planning of a diagnostic or therapeutic procedure.

Similarly with respect to the customizing of diagnostic and therapeutic devices for specific patients, there is no mechanism by which patient-specific devices can be rapidly prototyped by drawing upon designs that have generally proved successful with other patients. The lack of an efficient mechanism for customizing a generally successful design of a diagnostic or therapeutic device to match the anatomical features of a specific patient hampers the rapid prototyping of patient-specific devices.

SUMMARY OF THE INVENTION

The present invention provides systems and related methods for efficiently and effectively formulating patient-specific plans for medical procedures and deriving designs for patient-specific medical devices. One aspect of the present invention is the morphing of stored parameters corresponding to a standard plan for a medical procedure or a standard design for a medical device. Using morphing techniques provided by the invention, a standard medical plan or medical device can be adapted to a specific patient.

A particular benefit provided by the invention is that cumulative knowledge gained from the experiences of many other clinicians across a broad range of clinical practices can be leveraged, thereby enabling a physician to more rapidly and with more confidence arrive at a first, best-guess estimate in formulating a medical plan or device design for a particular patient. The morphing techniques provided by the invention, moreover, obviate the need for a physician to formulate a medical plan or device design anew for each patient.

One embodiment of the invention is a system for assisting in the formulation of a patient-specific plan for performing a diagnostic or therapeutic procedure upon a patient. The system can include a database containing at least one standard plan for performing a medical procedure. The plan can be based upon a scan of an anatomy of a standard anatomic specimen, the scan defining a standard scan. The system further can include a processor for processing data based upon a patient-specific scan of an anatomy of the patient. More particularly, the processor can process the data so as to morph a standard scan to the anatomy of the patient. The morphing is effected by the processors mapping the standard scan to the patient-specific scan. The patient-specific plan can then be formulated by modifying the standard plan based upon the mapping.

Another embodiment of the invention is a system for facilitating the design of a patient-specific medical device. The system can include a database containing at least one standard design for a medical device, the at least one device design can be based upon a scan of an anatomy of a standard anatomic specimen, the scan defining a standard scan. The system can further include a processor for processing data based upon a patient-specific scan of an anatomy of the patient. By processing the data, the processor can morph the standard scan to the anatomy of the patient by mapping the standard scan to the patient-specific scan. The design of the patient-specific device can be obtained by modifying the standard design based upon the mapping.

Yet another embodiment of the invention is a method for formulating a patient-specific plan for a diagnostic or therapeutic procedure performed upon a patient. The method can include obtaining a standard plan based upon a scan of an anatomy of a standard anatomic specimen, the scan defining a standard scan. Additionally, the method can include scanning the patient to obtain a patient-specific scan of an anatomy of the patient. The method also can include morphing the standard scan to the anatomy of the patient by mapping the standard scan to the patient-specific scan. The method further can include determining the patient-specific plan by modifying the standard plan based upon the mapping.

Still another embodiment of the invention is a method for designing a patient-specific device. The method can include providing a standard design of a device, the design based upon a scan of an anatomy of a standard anatomic specimen, the scan defining a standard scan. The method also can include scanning the patient to obtain a patient-specific scan of an anatomy of the patient. Additionally, the method can include morphing the standard scan to the anatomy of the patient by mapping the standard scan to the patient-specific scan. The method further can include determining a design of a patient-specific device by adapting the standard plan to the anatomy of the patient based upon the mapping based upon the mapping.

Yet another embodiment of the invention is a method for aligning a patient for performing a diagnostic or therapeutic procedure using an image guide. The method can include performing a first scan of the patient to obtain a first image of an anatomy of the patient positioned for a standard examination, the first image defining a first scan. The method further can include performing a second scan of the patient to obtain second image of the anatomy of the patient positioned for performing the procedure using the image guide, the second image defining a second scan. Additionally, the method can include morphing the first scan to the anatomy of the patient positioned for performing the procedure, the morphing effected by mapping the first scan to the second scan. The method further can include aligning the patient for performing the procedure using the image guide based upon the mapping.

Still another embodiment of the invention is a method of formulating a patient-specific plan for a diagnostic or therapeutic procedure performed upon a patient based upon data corresponding to an anatomy of a standard anatomical model. The method can include obtaining a standard plan based upon the data corresponding to the standard anatomical model, the data defining standard data. The method also can include scanning the patient to obtain a patient-specific scan of an anatomy of the patient. Additionally, the method can include morphing the standard data to the anatomy of the patient by mapping the standard data to the patient-specific scan. The method further can include determining the patient-specific plan by modifying the standard plan based upon the mapping.

DETAILED DESCRIPTION

One aspect of the present invention is the morphing of stored parameters corresponding to a standard plan for a medical procedure or a standard design for a medical device. As will be apparent from the exemplary embodiments described herein, through the morphing techniques provided by the invention, a standard medical plan or medical device can be adapted to a specific patient.

A benefit of this approach is that a physician can leverage the cumulative knowledge gained from the experiences of many other clinicians across a broad range of clinical practices. Leveraging this cumulative knowledge, a physician can more rapidly and with more confidence arrive at a first, best-guess estimate in formulating a medical plan or device design for a particular patient. The morphing techniques provided by the invention, moreover, obviate the need for a physician to formulate a medical plan or device design anew for each patient. Rather, the physician can arrive at a plan or design that is optimal for a particular patient by adapting known successful medical plans and device designs to the anatomy of each particular patient.

Figure 1:
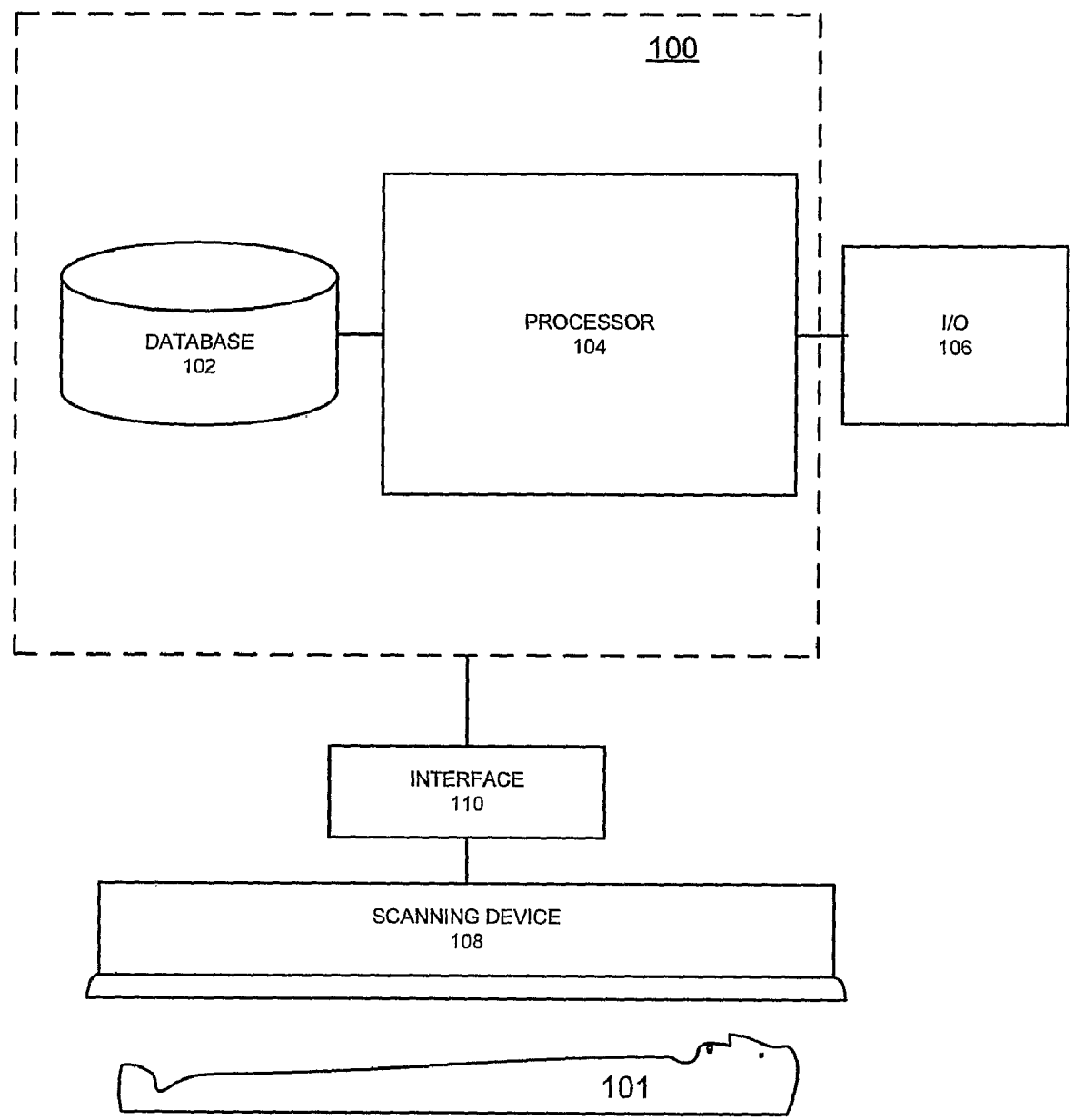
FIG. 1 is a schematic diagram of a system for facilitating medical planning, according to one embodiment of the invention.

FIG. 1 is a schematic diagram of a system 100 for assisting in the formulation of a patient-specific plan for performing a diagnostic or therapeutic procedure upon a patient 101, according to one embodiment of the invention. The system 100 illustratively includes a database 102 and a processor 104 communicatively linked to one another.

The database 102 contains one or more standard plans for performing a medical procedure. The one or more standard plans, according the invention, are each based upon a scan of an anatomy of a standard anatomic specimen. The scan of an anatomy of a standard anatomic specimen is here defined as a standard scan.

Various known scanning techniques can be employed to obtain a standard scan. Among these are computed/computerized tomography (CT), which is a diagnostic imaging procedure that combines computer processing and x-rays to present cross-sections of "slices" of the anatomic specimen. More particularly, the radiographic images produced by the CT scan provide a three dimensional image of a body structure, which, as will be readily understood by one of ordinary skill, is constructed by the computer from a series of plane cross-sectional images taken along an axis by the x-ray device. Yet another scanning technique is based on magnetic resonance imaging (MRI). MRI scans are obtained by ensconcing the specimen within the magnetic field generated by a magnet and detecting internal structures whose different content of atoms have certain resonances to the induced magnetic field, as will also be readily understood by one of ordinary skill. The result of the MRI, as with the CT scan, is a picture built up of one or more of a series of cross-sections of the anatomy of the specimen.

Some scanning techniques, such as cone beam CT scanning, provide non-contrast scans having less tissue differentiation than is typically needed for target localization. Nonetheless, such a scanning technique does provide a scan that is sufficient for determining the anatomic contours of a particular specimen. Accordingly, depending on the particular plan that is to be formulated, different techniques of scanning can be employed in carrying out the invention.

As already noted, one or more standard plans contained in the database 102 are each based upon a scan of the anatomy of a standard anatomic specimen, the scan defining a standard scan. An objective of using a standard scan is to formulate an optimal plan for a standard or baseline patient. For example, in the context of a plan for fitting a stereotactic frame to a patients head, the plan can be formulated based on the size and dimension of a normal or average human head. Similarly, in the context of determining the entry point and trajectory for inserting a device such as an image guide or pedicle screw into a patient, a standard plan for optimally performing the procedure can be formulated on the basis of the bony structure of the normal or average patient.

Thus, according to the invention, each of the one or more standard plans contained in the database 102 can be based on a scan of the anatomy of a standard anatomic specimen, the specimen being, for example, a human of a certain age and/or sex who exhibits certain predetermined baseline or average anatomical features and characteristics. The standard anatomic specimen also can be derived from a standard model, such as that of a standard model of an adult human. Thus, according to an alternative embodiment, database 102 can contain data corresponding to a standard anatomical model.

Regardless of the particular medical procedure to be performed, the system 100 can generate or assist in the formulation of a plan for performing the procedure on a particular patient 101. In effecting this outcome, the processor 104 of the system processes data based on, or derived from, a scan of the anatomy of the patient 101, the scan defining a patient-specific scan. The processor 104 processes this data in order to morph the standard scan to the anatomy of the patient 101. More particularly, the processor 104 maps the standard scan to the patient-specific scan by altering the parameters that characterize the scan-determined standard anatomy structure to conform to or more closely match that those that characterize anatomy of the patient, as determined by the scan of the anatomy of the patient.

The terms morph and morphing are used herein in their broadest sense and refer generally to transformations by which one image is transformed to another by the distortion of corresponding points. As will be readily understood by one of ordinary skill, a continuous deformation from one key-frame or three-dimensional (3-D) model to another can be effected through morphing. In the context of a 3-D model or image, morphing can be achieved by approximating a surface with a triangular mesh that can then be continuously deformed. In the context of a two-dimensional (2-D) image or model, morphing can be generally performed by either distortion or deformation.

According to one particular embodiment, the mapping is accomplished by the processor 104 performing a non-rigid deformation of the standard scan. As already described, various known scanning techniques can be used to obtain scans of a standard anatomy structure. The processor 104, according to this embodiment, implements one or more known non-rigid deformation algorithms that "deform" the standard scan so that it match the parameters or otherwise conforms to the shape of the scan obtained by scanning the patient 101. Known techniques underlying these algorithms include, for example, mesh warping, mapping of mesh vertices, warping based upon thin plate spline (TPS) transformations, and various other techniques for performing non-rigid deformations.

Figure 2:
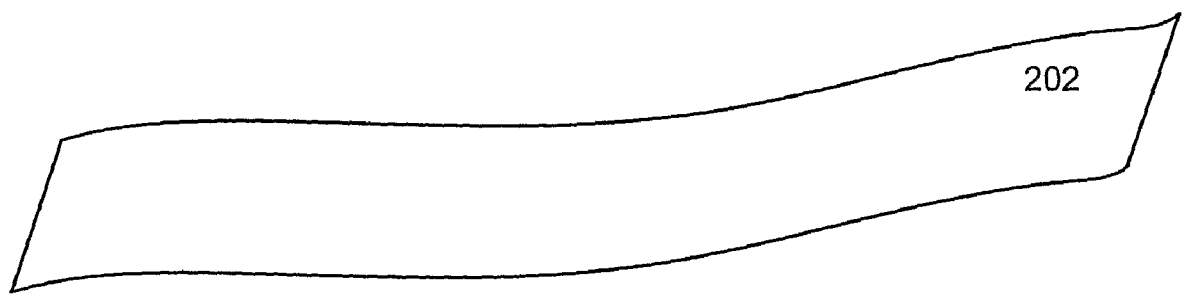
FIG. 2 is a schematic diagram of a non-rigid deformation mapping of a standard scan to a patient-specific scan, according to another embodiment of the invention.
Figure 2:
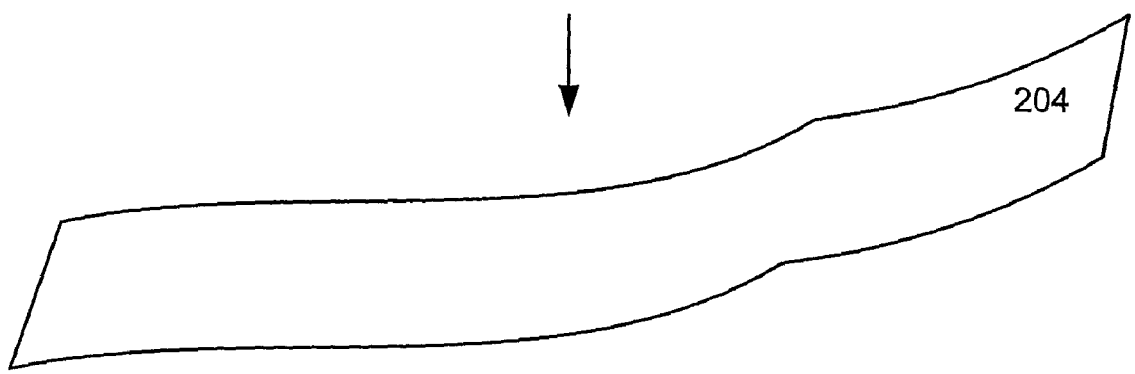
Figure 2:
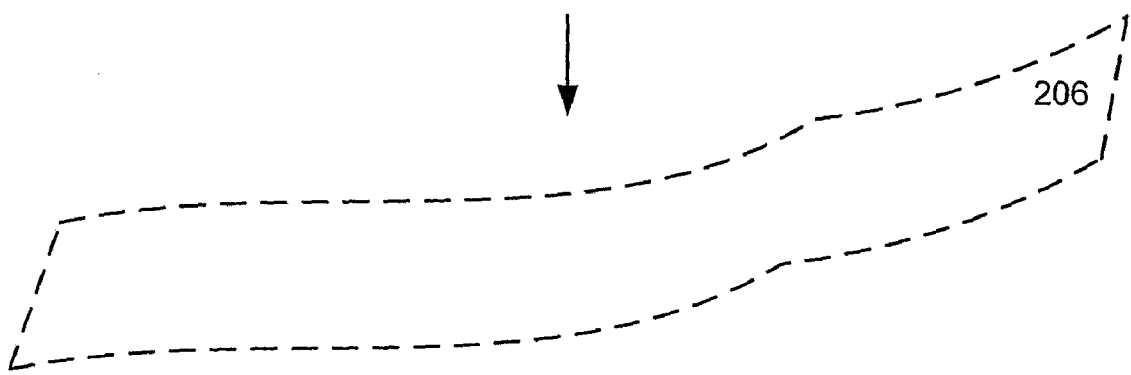

The effect of a mapping 200 based upon a non-rigid deformation, which maps a standard scan to a patient-specific scan, is schematically illustrated in FIG. 2. The standard scan 202 can comprise a region of the anatomy of the standard anatomic specimen. The patient-specific scan 204, accordingly, comprises a corresponding region of the anatomy of the patient 101. The processor 104, as described, implements an algorithm or procedure that conforms the standard scan to the patient-specific scan by manipulating or changing the parameters of the latter, the result being the conformed scan 206. Although not explicitly illustrated, each of the scans can comprise a plurality of regular or irregular segments having determined vertices. Thus, for example, one mode of mapping the standard scan 202 to the patient-specific scan 204 is to adjust the vertices of the former to match those of the latter.

As already noted, the database 102 alternatively, or additionally, can comprise data corresponding to a standard anatomical model. Accordingly, the processor 104 can be configured to map a patient-specific scan to the data corresponding to the standard anatomical model to morph the standard data to the anatomy of a particular patient.

Although the invention is described herein primarily in terms of mappings based upon non-rigid deformations, in alternative embodiments the mapping can be based upon rigid deformations. Various algorithms can be implemented by the processor 104 for effecting mappings of the standard scan to the patient-specific scan. These algorithms can be based, for example, on mappings using an affine transformation or various other techniques for image deformation.

The mapping of the standard scan to the patient-specific scan by the processor 104, as described, yields a set of parameters that conform to or otherwise match the anatomy of the specific patient 101. Based on these parameters, the patient-specific plan can be formulated. Specifically, the patient-specific plan can be formulated by modifying the standard plan according to the set of parameters resulting from the mapping. Accordingly, the patient-specific plan is a modification or adjustment of the standard plan based upon the mapping.

The processor 104 can be implemented with dedicated hardwired circuitry for performing the procedures described herein. Alternatively, the processor 104 can be an application-specific or general-purpose computing device on which resides a set of machine-readable code for carrying out these procedures. In yet another embodiment, the processor 104 comprises a combination of hardwired circuitry and machine-readable code that cooperatively perform various processing functions for effecting the procedures described herein.

The system 100, according to another embodiment, is configured to receive input and convey output via an input-output (I/O) device 106, such as combination of a keyboard and visual display. Thus, according to this embodiment, patient-specific data obtained from a scan of the patient 101 can be supplied to the system 100 for processing via the I/O device 106. Accordingly, the system 100 need not be co-located with a scanning device, but rather can be remote from the location where the patient-specific scan is obtained. The corresponding patient specific data can be supplied directly by a user of the I/O device 106 or indirectly via a data communications network, such as the Internet or a local area network (LAN), by a user of a remote terminal.

Alternatively, or additionally, the system 100 can be configured to receive patient-specific scan data from a scanning device 108. Optionally, an interface 110 can be interposed between the system 100 and the scanning device 108. The interface 110 can be configured to convert analog signals rendered by the scanning device 108 into digital signals amenable to processing by the processor 104 using, for example, discrete-time Fourier transforms (DTFT) or other digital signal processing techniques.

According to still another embodiment, the system 100 facilitates the design of a patient-specific medical device. The database 102, according to this embodiment, contains one or more standard designs for medical devices. The one or more standard designs, more particularly, can be based upon a scan of an anatomy of a standard anatomic specimen.

The processor 104 processes data based upon a patient-specific scan of an anatomy of the patient, as described above. More particularly, the processor 104 processes the data so as to morph the standard scan to the anatomy of the patient by mapping the standard scan to the patient-specific scan. The design of the patient-specific device can then be obtained by modifying the standard design based upon the mapping.

According to an alternative embodiment, the standard device design can be based on data corresponding to a standard anatomical model. Thus, in this alternative embodiment, the processor 104 morphs the standard data to the anatomy of the patient by mapping the standard data to the patient-specific scan, as described in the earlier context of medical planning.

Figure 3:
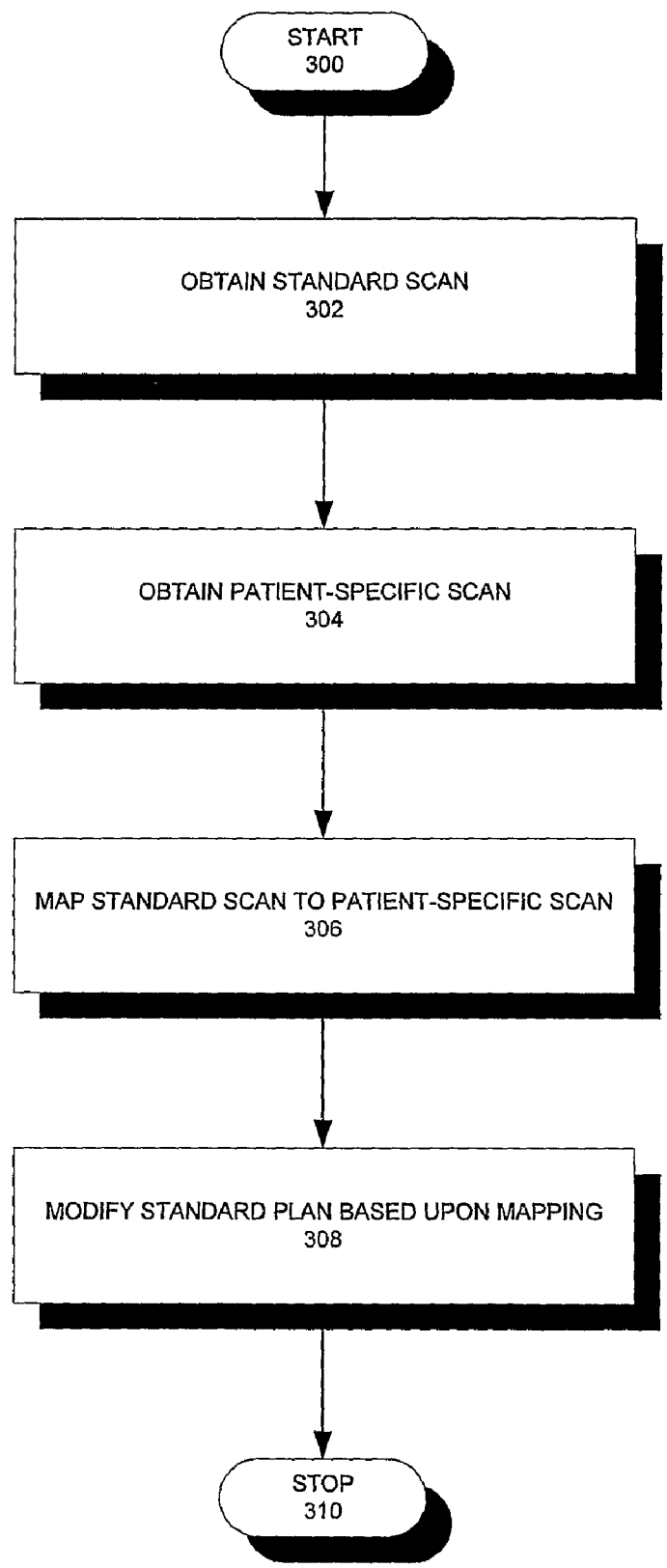
FIG. 3 is a flow chart of the exemplary steps of a method for formulating a patient-specific plan for a diagnostic or therapeutic procedure performed upon a patient, according to yet another embodiment of the invention.

FIG. 3 is a flow chart of a method 300 for formulating a patient-specific plan for a diagnostic or therapeutic procedure performed upon a patient. Illustratively, the method 300 includes, at step 302, obtaining a standard plan. The standard plan, more particularly, can be based upon a scan of an anatomy of a standard anatomic specimen, the scan defining a standard scan. Alternatively, the standard plan can be based upon data corresponding to a standard anatomical model.

The method 300 further includes, at step 304, obtaining a patient-specific scan of an anatomy of the patient. The patient-specific scan can be obtained by performing a scan of the patient to obtain an image of the anatomy of the patient.

At step 306 of the method, the standard scan is mapped to the patient-specific scan. Alternatively, in the event that data based upon a standard anatomical model is utilized in lieu of a standard scan, it is this data based upon the standard anatomical model, defining standard model data, that is mapped to the patient-specific scan at step 306. The mapping results in a morphing of the standard scan or data so as to align with or more closely match the anatomy of the patient. The patient-specific plan is determined at step 308 by modifying the standard plan based upon the mapping. The method 300 illustratively concludes at step 310.

The mapping at step 306, according to one embodiment, is based upon a non-rigid deformation of the standard scan. According to an alternative embodiment, however, the mapping at step 306 is based upon a rigid deformation of the standard scan.

The determination of the patient-specific plan at step 308, more particularly, can comprise determining a selection of a specific anatomic region of the patient for examination. Alternatively, or additionally, the determination of the patient-specific plan at step 308 can comprise determining an alignment relative to an anatomical feature of the anatomy of the patient of at least one of a diagnostic device and a therapeutic device. Moreover, determining the patient-specific plan at step 308 can alternatively, or additionally, comprise determining a path relative to anatomical features of the anatomy of the patient for inserting at least one of a diagnostic device and a therapeutic device into the anatomy of the patient. In each event, the standard plan needs only be modified to the extent necessary to accommodate the particular anatomical features of the patient as revealed by the mapping of the standard scan to the patient-specific scan.

Figure 4:
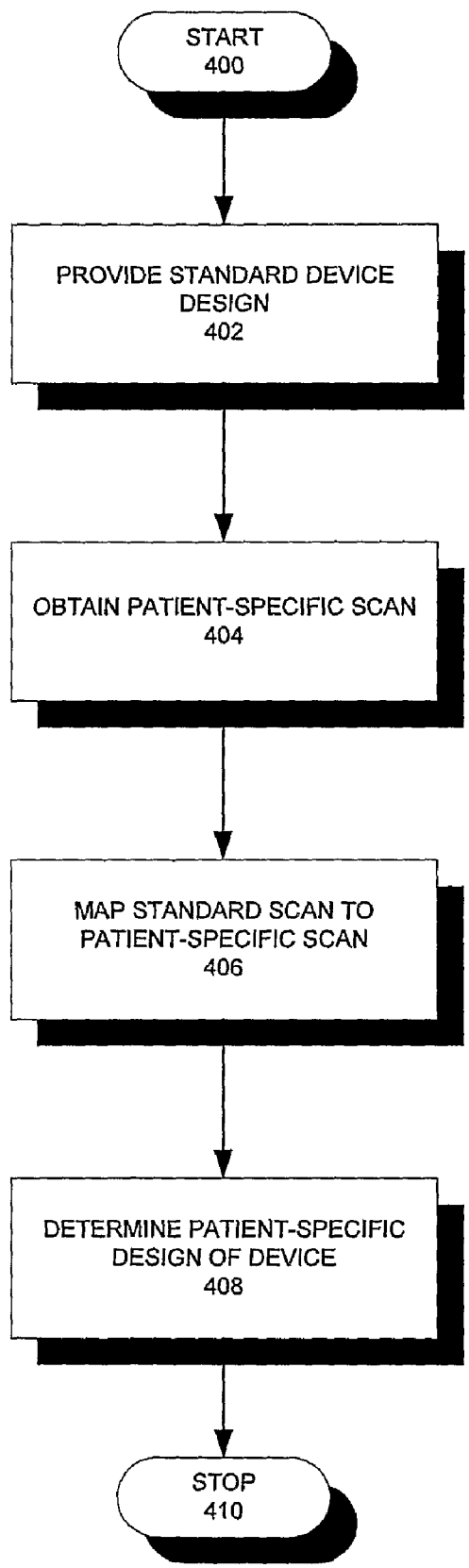
FIG. 4 is a flow chart of the exemplary steps of a method for facilitating the design of a patient-specific medical device, according to still another embodiment of the invention.

FIG. 4 is a flow chart of the exemplary steps of a method 400 for facilitating the design of a patient-specific medical device, according to still another embodiment of the invention. The method 400 includes, at step 402, providing a standard design of the device. The design, moreover, can be based upon a scan of the anatomy of a standard anatomic specimen, the scan defining a standard scan. Alternatively, the design can be based upon data corresponding to a standard anatomical model.

The method 400 further includes obtaining a patient-specific scan of the anatomy of the patient at step 404. The patient-specific scan can be obtained by scanning the patient using an imaging device. Additionally, the method 400 includes, at step 406, mapping the standard scan to the patient-specific scan. The mapping can be used to morph the standard scan to the anatomy of the patient. If, instead, the standard device design is based upon data corresponding to a standard anatomical model, the data corresponding to the standard anatomical model, defining standard model data, is mapped to the patient-specific scan at step 406.

At step 408, the design of a patient-specific device is determined based upon an adaptation of the standard plan to the anatomy of the patient based upon the mapping based upon the mapping. The method illustratively concludes at step 410.

According to a particular embodiment, the mapping at step 406 is based upon a non-rigid deformation of the standard scan. The mapping at step 406, however, can alternatively be based upon a rigid deformation of the standard scan according to an alternative embodiment.

The step 408 of determining the design of a patient-specific device can comprise determining a design such that the device is effectively used in a specific anatomic region of the patient. Additionally, or alternatively, the determination of the design at step 408 can comprise determining a design that aligns the device properly relative to an anatomical feature of the anatomy of the patient. Determining the design of a patient-specific device at step 408, alternatively or additionally, can comprise determining a design that allows the device to be used along a predetermined path relative to anatomical features of the anatomy of the patient, the device being a diagnostic device or a therapeutic device inserted into the anatomy of the patient.

Figure 5:
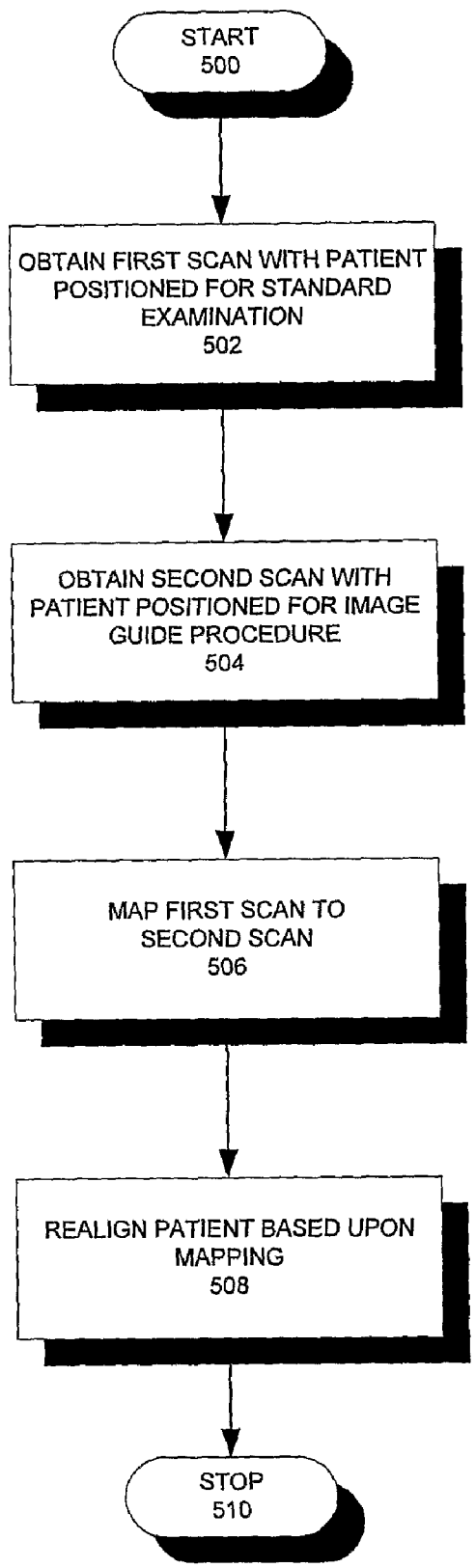
FIG. 5 is a flow chart of the exemplary steps of a method for positioning a patient for performing a procedure using an image guide, according to yet another embodiment of the invention.

FIG. 5 is a flow chart of the exemplary steps of a method, according to yet another embodiment of the invention, for positioning a patient on whom a procedure using an image guide is to be performed. The method 500 includes, at step 502, performing a first scan of the patient to obtain a first image of an anatomy of the patient, wherein the patient is positioned for a standard examination. The first image defines a first scan.

At step 504, the method 500 includes performing a second scan of the patient to obtain second image of the anatomy of the patient, wherein the patient is positioned for performing the procedure using the image guide. The second image defines a second scan. The first scan is mapped to the second scan in step 506, according to the method 500. The mapping morphs the first scan to the anatomy of the patient when the patient is positioned for performing the procedure. At step 508 of the method 500, the patient is aligned for performing the procedure using the image guide based upon the mapping. The method 500 illustratively concludes at step 510.

The mapping of the first scan to the second scan at step 506, according to a particular embodiment, can be based upon a non-rigid deformation of the first scan. Alternatively, the mapping of the first scan to the second scan at step 506 can be based upon a rigid deformation of the first scan. According to yet another embodiment, the first and second scans can be performed using different scanning devices. Accordingly, the first scan can be obtained using a device particularly suited for imaging the patient when the patient is positioned for an examination, whereas the second scan can be obtained using a device especially suited for imaging the patient when the patient is positioned to accommodate the procedure using an image guide.

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is being claimed:

1. A method of formulating a patient-specific plan for a diagnostic or therapeutic procedure to be performed upon a patient, the method comprising the steps of:

obtaining a standard plan based upon a model of an anatomy of a human specimen having average anatomical features and characteristics, the model defining a standard model;

scanning the patient prior to performing the procedure to obtain a patient-specific scan of an anatomy of the patient;

morphing the standard model to the anatomy of the patient by mapping the standard model to the patient-specific scan; and determining the patient-specific plan by modifying the standard plan based upon the mapping.

2. The method of claim 1, wherein the mapping is based upon a non-rigid deformation of the standard model.

3. The method of claim 1, wherein the mapping is based upon a rigid deformation of the standard model.

4. The method of claim 1, wherein the step of determining the patient-specific plan comprises determining a selection of a specific anatomic region of the patient for examination.

5. The method of claim 1, wherein determining the patient-specific plan comprises determining an alignment relative to an anatomical feature of the anatomy of the patient of at least one of a diagnostic device and a therapeutic device.

6. The method of claim 1, wherein determining the patient-specific plan comprises determining a path relative to anatomical features of the anatomy of the patient for inserting at least one of a diagnostic device and a therapeutic device into the anatomy of the patient.

7. The method of claim 1, wherein the standard model is a scan of a human being who exhibits predetermined baseline or average anatomical features and characteristics.

8. A method for designing a patient-specific device to be used in performing a diagnostic or therapeutic procedure on a patient, the method comprising the steps of:

providing a standard design of a device, the design based upon a model of an anatomy of a human specimen having average anatomical features and characteristics, the model defining a standard model;

scanning the patient prior to performing the procedure to obtain a patient-specific scan of an anatomy of the patient;

morphing the standard model to the anatomy of the patient by mapping the standard model to the patient-specific scan; and determining a design of a patient-specific device by adapting the standard design to the anatomy of the patient based upon the mapping.

9. The method of claim 8, wherein the mapping is based upon a non-rigid deformation of the standard model.

10. The method of claim 8, wherein the mapping is based upon a rigid deformation of the standard model.

11. The method of claim 8, wherein the step of determining the design of a patient-specific device comprises determining a design for a device that is used in a specific anatomic region of the patient.

12. The method of claim 8, wherein determining the design of a patient-specific device comprises determining a design that aligns the device properly relative to an anatomical feature of the anatomy of the patient.

13. The method of claim 8, wherein determining the design of a patient-specific device comprises determining a design for a device that is used along a predetermined path relative to anatomical features of the anatomy of the patient, the device being a diagnostic device or a therapeutic device inserted into the anatomy of the patient.

14. The method of claim 8, wherein the standard model is a scan of a human being who exhibits predetermined baseline or average anatomical features and characteristics.

15. A system for assisting in the formulation of a patient-specific plan for a diagnostic or therapeutic procedure to be performed upon a patient, the system comprising:

a database containing at least one standard plan for performing a medical procedure, the at least one standard plan being based upon a model of an anatomy of a human specimen having average anatomical features and characteristics, the model defining a standard model; and a processor for processing data based upon a pre-operative patient-specific scan of an anatomy of the patient, wherein the processor processes the data to morph the standard model to the anatomy of the patient by mapping the standard model to the patient-specific scan, and wherein the patient-specific plan is formulated by modifying the at least one standard plan based upon the mapping.

16. The system of claim 15, wherein the at least one standard plan comprises a plurality of standard plans, including at least one of identifying and extracting targeted tissue from the patient for performing a biopsy, identifying a point of entry into and path of trajectory within the patient for placing a medical device, and aligning a patient for performing a procedure using an image guide.

17. The system of claim 15, wherein the standard model is a scan of a human being who exhibits predetermined baseline or average anatomical features and characteristics.

18. A system for facilitating the design of a patient-specific medical device, the system comprising:

a database containing at least one standard design for a medical device, the at least one standard design being based upon a model of an anatomy of a human specimen having average anatomical features and characteristics, the model defining a standard model; and a processor for processing data based upon a pre-operative patient-specific scan of an anatomy of a patient, wherein the processor processes the data to morph the standard model to the anatomy of the patient by mapping the standard model to the patient-specific scan, and wherein the design of the patient-specific device is obtained by modifying the at least one standard design based upon the mapping.

19. The system of claim 18, wherein the at least one standard design comprises a plurality of standard designs, including at least one of a design for a device used for performing a biopsy, a design for a device used for obtaining an image, and a design for a prosthetic device.

20. The system of claim 18, wherein the standard model is a scan of a human being who exhibits predetermined baseline or average anatomical features and characteristics.

* * * * *